(12) United States Patent
Chen et al.

(10) Patent No.: US 9,651,521 B2
(45) Date of Patent: May 16, 2017

(54) MICROSECOND TIME-RESOLVED MASS SPECTROMETRY

(71) Applicant: Ohio University, Athens, OH (US)

(72) Inventors: Hao Chen, Athens, OH (US); Zhixin Miao, Athens, OH (US)

(73) Assignee: Ohio University, Athens, OH (US)

(*) Notice: Subject to any disclaimer, the term of this patent is extended or adjusted under 35 U.S.C. 154(b) by 0 days.

(21) Appl. No.: 14/818,404

(22) Filed: Aug. 5, 2015

(65) Prior Publication Data

US 2015/0338375 A1    Nov. 26, 2015

Related U.S. Application Data (62) Division of application No. 13/697,621, filed as application No. PCT/US2011/036736 on May 17, 2011.

(60) Provisional application No. 61/345,256, filed on May 17, 2010.

(51) Int. Cl.

| | |
|---|---|
| G01N 27/68 | (2006.01) |
| H01J 49/16 | (2006.01) |
| H01J 49/04 | (2006.01) |
| G01N 33/68 | (2006.01) |
| G01N 1/00 | (2006.01) |
| H01J 49/14 | (2006.01) |
| G01N 33/487 | (2006.01) |

(52) U.S. Cl.
CPC ............ *G01N 27/68* (2013.01); *G01N 1/00* (2013.01); *G01N 33/48707* (2013.01); *G01N 33/6848* (2013.01); *H01J 49/045* (2013.01); *H01J 49/0445* (2013.01); *H01J 49/145* (2013.01); *H01J 49/165* (2013.01)

(58) Field of Classification Search
CPC ...... G01N 1/00; G01N 33/6848; G01N 27/68; G01N 33/48707; H01J 49/0445; H01J 49/145; H01J 49/045; H01J 49/165
USPC .......................................................... 436/34
See application file for complete search history.

(56) References Cited

U.S. PATENT DOCUMENTS

| | | | | |
|---|---|---|---|---|
| 6,054,709 A | * | 4/2000 | Douglas .............. | H01J 49/0431 250/282 |
| 6,870,154 B1 | * | 3/2005 | Konermann ........ | H01J 49/0431 250/281 |
| 7,462,825 B2 | * | 12/2008 | Miller .................. | G01N 27/624 250/281 |
| 2010/0059674 A1 | * | 3/2010 | Chen .................... | H01J 49/145 250/288 |

* cited by examiner

Primary Examiner — Rebecca M Fritchman
(74) Attorney, Agent, or Firm — Wood Herron & Evans LLP (57) ABSTRACT

A microsecond time-resolved mass spectrometry device and method of using desorption electrospray ionization (10) was described for the kinetic study of fast reactions. The device includes a liquid jet generator (64) that is configured to emit a continuous liquid jet (50) having a length. An ambient ionization source (10) is directed toward a selected variable location along the continuous liquid jet (50) to desorb at least a portion of the continuous liquid jet (50). A mass analyzer (30) analyzes a mass-to-charge ratio of an ionized sample that is within the desorbed portion of the continuous liquid jet (50). The acquired mass spectra reflect the reaction progress in different reaction times and, therefore, may be used to derive the reaction rate.

10 Claims, 8 Drawing Sheets

MICROSECOND TIME-RESOLVED MASS SPECTROMETRY

RELATED APPLICATION

This application is a divisional of and claims benefit to U.S. patent application Ser. No. 13/697,621, which is a United States National Phase application based on PCT/US2011/036736, which claims priority to U.S. provisional patent application Ser. No. 61/345,256, the disclosures of which are incorporated herein by reference as if set out fully herein in their entirety.

GOVERNMENT FUNDING

This invention was made with government support under 0911160 awarded by the National Science Foundation. The government has certain rights in the invention.

TECHNICAL FIELD

The invention is with regard to the apparatus and methodology of time-resolved mass spectrometry.

BACKGROUND OF THE INVENTION

Chemical kinetics is the study of rates at which a chemical reaction occurs. Such an investigation provides understanding of the reaction mechanisms along with the identification of possible reaction intermediates.

Of particular interest are biochemical reactions, such as protein conformational change and enzymatic catalysis, which are responsible for many important biochemical and physiological processes. The protein conformational changes or the formation of enzyme-substrate complex intermediates may occur within microseconds, making the detection of intermediates technically challenging.

Conventional techniques for kinetic study generally involve spectroscopic methods, such as UV and fluorescence spectroscopy. These methods have the benefit of high time resolution, for example, femtosecond or attosecond time scales. However, these techniques also require chromophoric substrates or radioactive labeling.

Mass spectrometry (MS)-based approaches to study kinetics are being developed, particularly with the advent of electrospray ionization (ESI). Notably, the time-resolved ESI-MS work based on elegant designs for reactant solution mixing have been established to allow the monitoring of reaction kinetics with time resolution ranging from milliseconds to seconds.

The striking advantages of using conventional MS detection over spectroscopic detection are that conventional MS has high chemical specificity and does not require chromophoric substrates. Nevertheless, it is necessary to further improve the time resolution of MS methods, which is required for MS kinetic study, to help to capture the possible intermediate and to investigate the mechanism of fast reaction processes.

SUMMARY OF THE INVENTION

In one illustrative embodiment, the present invention is directed to microsecond time-resolved mass spectrometry. The time-resolved mass spectrometry device includes a liquid jet generator that is configured to emit a continuous liquid jet having a length. An ambient ionization source is directed toward a selected variable location along the length of the continuous liquid jet to desorb at least a portion of the continuous liquid jet. A mass analyzer analyzes a mass-to-charge ratio of an ionized sample that is within the desorbed portion of the continuous liquid jet.

In another illustrative embodiment, the present invention is directed to a mass spectrometer system having an ion source that includes first and second sample sources, a mixer, and a nebulizing ionizer. The system also includes a mass analyzer that is configured to analyze a mass-to-charge ratio of an ionized sample that is desorbed from a continuous liquid jet that is ejected from the mixer. A controller is configured to operate an ion source of the nebulizing ionizer or the mass analyzer or both.

Yet another illustrative embodiment is directed to a method of calculating a rate constant of a reaction. The method includes supplying at least two reactants to the mixer and ejecting a mixture of the at least two reactants as a continuous liquid jet from the mixer. A nebulizing ionizer is positioned at a first distance along the continuous liquid jet such that at least a portion of the continuous liquid jet is desorbed as a first ionized sample. The first ionized liquid sample is directed to the mass analyzer where a relative abundance of the first ionized liquid sample is measured. The nebulizing ionizer is positioned at a second distance along the continuous liquid jet such that at least a portion of the continuous liquid jet is desorbed as a second ionized sample. The second ionized liquid sample is directed to the mass analyzer where a relative abundance of the second ionized liquid sample is measured. As the time interval between the ionization of two different jet positions is known, the relative abundances are then related for calculating the rate constant.

The objects and advantages of the present invention will be further appreciated in light of the following detailed description and drawings provided herein.

BRIEF DESCRIPTION OF THE DRAWINGS

The accompanying drawings, which are incorporated in and constitute a part of this specification, illustrate embodiments of the invention and, together with a general description of the invention given above and the detailed description given below, serve to explain the principles of the invention.

DETAILED DESCRIPTION

The present invention relates generally to time-resolved mass spectroscopy techniques using a liquid sample desorption electrospray ionization mass-spectrometry (LS-DESI-MS) apparatus. The LS-DESI-MS apparatus was described in detail in U.S. patent application Ser. No. 12/205,236 (now U.S. Pat. No. 7,915,579) and Ser. No. 12/558,819 (published as U.S. Patent Application Publication No. 2010/0258717), the disclosures of which are incorporated herein by reference in their entireties.

Figure 1A:
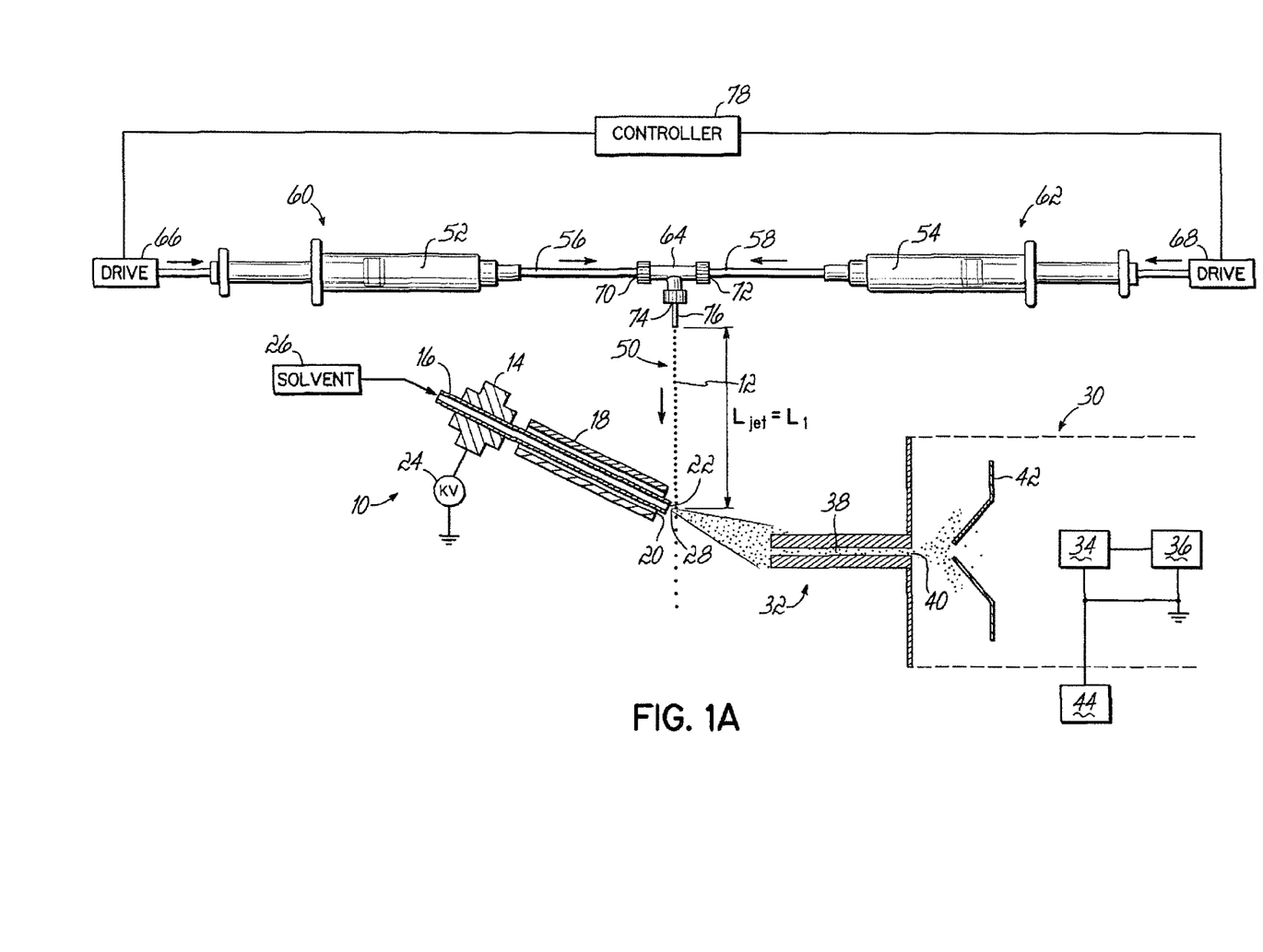
FIG. 1A is a schematic representation of one exemplary embodiment of an apparatus for time-resolved liquid jet desorption electrospray ionization mass spectroscopy study with a sampling distance of $L_1$.

Briefly, FIG. 1A illustrates the LS-DESI-MS apparatus having a nebulizing ionizer 10 for desorption and ionization of a sample 12. As shown, the nebulizing ionizer 10, a desorption electrospray ionization (DESI) probe, includes a housing 14 having a solvent conduit 16 surrounded by a gas conduit 18; however, it would be understood that any ambient ionization method apparatus could be used. An outlet 20 of the gas conduit 18 may be positioned about 0.1 mm to about 0.2 mm proximally to an outlet 22 of the solvent conduit 16. The solvent conduit 16 may be constructed from a fused silica capillary with an inner diameter of about 0.1 mm. The gas conduit 18 may also be a fused silica capillary with an inner diameter that is generally larger than the outer diameter of the solvent conduit 16, i.e., typically about 0.25 mm; however, these dimensions should not be considered limiting.

A voltage generator 24 is attached to the housing 14 and is operable to charge a solvent 26 that is pumped into the solvent conduit 16.

In using the DESI probe 10, the solvent 26 is supplied to the solvent conduit 16 at a rate ranging from about 5 μL/min to about 10 μL/min. The particular solvent 26 used is dependent on the chemical nature of the sample in study, and the manner by which to select an appropriate solvent is well known to those of ordinary skill in the art. A gas, typically an inert gas such as $N_2$, is supplied to the gas conduit 18 at pressures ranging from about 8 bar to about 12.5 bar. The voltage generator 24 is activated and provides a voltage potential, typically ranging from about −5 kV to about 5 kV, to the solvent 26 through the housing 14. This generates an electrically charged solvent within the solvent conduit 16.

The now electrically charged solvent 26 traverses the solvent conduit 16 to the solvent conduit outlet 22. There, the charged solvent 26 is impacted by the surrounding high-pressure gas leaving the gas conduit outlet 20. This high-pressure gas causes the flow of the charged solvent 26 to be nebulized into a spray 28 of charged and nebulized solvent, which then impacts the sample 12. This impact will cause desorption and ionization of a portion of the sample 12 into a mass analyzer 30. It will be readily appreciated that the angle by which the spray 28 impacts the sample 12 may be varied to increase the likelihood of the liquid sample 12 entering the mass analyzer 30.

While not wishing to be bound by theory, it is believed that the mechanism by which the spray 28 interacts with the sample 12 and desorbs at least a portion of the sample 12 may be chemical sputtering, charge transfer, or droplet pick-up, with the most likely of these mechanisms being droplet pick-up. During droplet pick-up, the spray 28 interacts with the sample 12 to yield desorbed secondary charged droplets containing analyte. The secondary charged droplet will then undergo desolvation to yield ions of the analyte, i.e., gas phase ions.

The mass analyzer 30 generally includes an interface 32 with the nebulizing ionizer 10, a mass filter 34, and a mass detector 36, which are maintained at vacuum. The interface 34 may aid in the desolvation of the secondary charged droplet, and accordingly, may include an inlet 38, which may consist of a heated capillary, leading to an orifice 40 so that an opening into the mass analyzer 30 is provided while maintaining vacuum pressures. The gas phase ions are then directed to a skimmer 42, which focuses the gas phase ions into a narrow beam (not shown) of ion beam entering the mass filter 34. In some embodiments, the mass analyzer 30 may further include a separate focusing lens (not shown) between the skimmer 42 and the mass filter 34 to further focus the ion beam and reduce the natural expansion of the ion beam.

The mass filter 34 may be any conventional mass filter 34 such as time-of-flight, quadrupole, sector, Orbitrap, Fourier Transform Ion Cyclotron Resonance, or ion trap, which are operable to cause gas phase ions having a specified mass-to-charge (m/z) ratio to transverse the mass filter 34 and be quantified at the mass detector 36. One particularly suitable instrument is the hybrid triple-quadrupole-linear ion trap mass spectrometer, Q-trap 2000, by Applied Biosystems/MDS Sciex (Concord, Canada).

In operation of a conventional quadrupole modality, an ion beam is directed through four parallel electrodes, wherein the four parallel electrodes are comprised of two pairs of electrodes. A radiofrequency field and a DC voltage potential are applied to each of the two pairs of electrodes by a power supply such that the two pairs differ in polarity of the voltage potentials. Only the ions within the ion beam having a first mass-to-charge ratio, $m_1/z_1$, will continue through the parallel electrodes to the mass detector 36; that is, the $m_1/z_1$ ions will be equally attracted to and deflected by the two pairs of electrodes while the mean free path induced by the radiofrequency field onto the $m_1/z_1$ ions does not exceed the distance between the electrodes. Thus, the $m_1/z_1$ ions will balance the radiofrequency and DC voltage forces from the parallel electrodes and traverse the parallel electrodes to impact the mass detector 36.

The $m_1/z_1$ ions that reach the mass detector 36, typically a Faraday plate coupled to a picoammeter, are measured as a current (I) induced by a total number (n) of ions impacting the mass detector 36 over a period of time (t) and in accordance with n/t=I/e, wherein e is the elementary charge.

The method continues with altering the operational conditions of the mass filter 34 such that ions having a second mass-to-charge ratio, $m_2/z_2$, will traverse the mass filter 34 and impact the mass detector 36 in the manner described. A spectrum may then be generated relating the relative abundancies with respect to m/z of the ions detected.

Operation of the mass filter 34 and the mass detector 36 may include a controller 44. A suitable controller 44 can be a standard PC computer; however, the present invention should not be considered so limited.

To effectuate the use of LS-DESI-MS for microsecond time resolution kinetic study, a liquid jet 50 of the sample 12 is generated. In that regard, and in order to provide ultrafast mixing of at least two reactants 52, 54, separate reactant sources, shown herein as capillaries 56, 58 extending from each of at least two syringes 60, 62 containing one of the at least two reactants 52, 54, are coupled with a mixer 64. The at least two syringes 60, 62 may include any appropriate volume, commercially-available syringe, such as the Model 1750 series from Hamilton Co. (Reno, Nev.). As shown, the at least two syringes 60, 62 may be of the same type; however, this is not necessary.

It would be readily appreciated that while a T-shaped mixer 64 ("Tee-mixer") is specifically shown, other mixer shapes are possible, including Y-shaped or other shapes having multiple inlets such that more than two reactants may be used.

The syringes 60, 62 may be automatically driven to supply a constant flow of the reactants 52, 54 to the Tee-mixer 64, for example, at a rate of about 200 μL/min. The driving may be accomplished by syringe pumps 66, 68, for example, Fusion 100 syringe pumps from Chemyx, Inc. (Stafford, Tex.); however, other pumps or devices may be used. Alternatively, a High Performance Liquid Chromatograph (HPLC) pump may be used to introduce the reactant solution with a higher flow rate for generating a high-speed jet.

First and second ends 70, 72 of the Tee-mixer 64 receive the capillaries 56, 58 while a third end 74 of the Tee-mixer 64 includes an outflow capillary 76. The at least two reactants 52, 54 meet and mix within the Tee-mixer 64 and the outflow capillary 76 and are ejected as the continuous liquid jet 50 of sample 12. The outflow capillary 76 may be constructed from a deactivated fused silica capillary with an inner diameter and length selected to provide a desired dead volume for mixing. For example, a 50 μm inner diameter outflow capillary 76 having a length of 3 cm would provide a dead volume of 60 nL. A mixing dead time may be calculated from the dead volume and the flow rate of the at least two reactants 52, 54, and in the instant example is calculated to be 9 ms.

Though not particularly shown, the at least two syringes 60, 62 and the Tee-mixer 64 may be supported on a vertically translatable apparatus, such as a ring stand coupled to a lab jack, to enable the LS-DESI-MS sampling of the liquid jet 50 as provided in greater detail below.

Figure 1B:
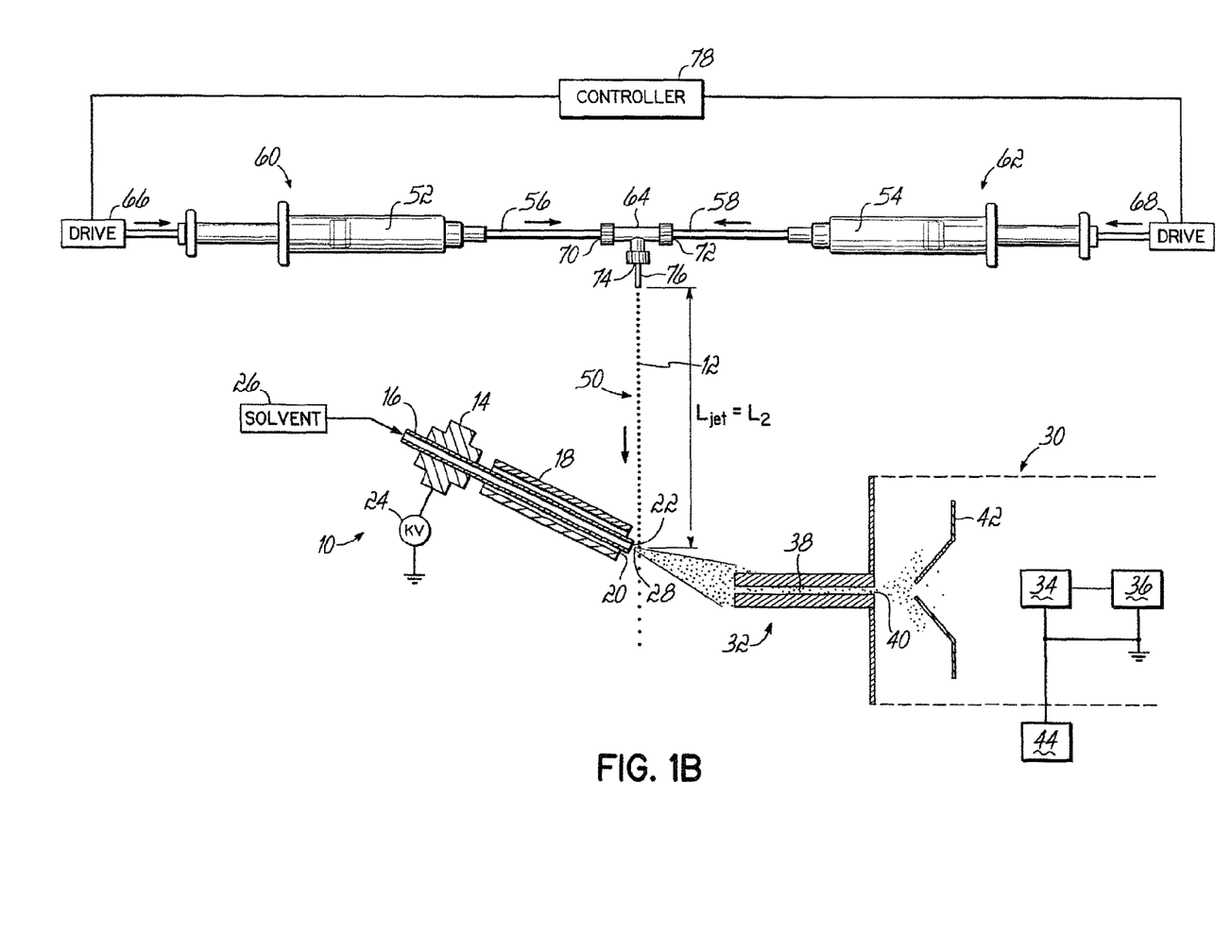
FIG. 1B is a schematic representation of the apparatus of FIG. 1A with the sampling distance of $L_2$.

It would be understood that at least one reaction between the at least two reactant 52, 54 begins at mixing within the Tee-mixer 64 and proceeds as the liquid jet 50 emerges from the outflow capillary 76. In this way, reaction time may be correlated to a linear distance, $L_{jet}$. Thus, desorption and ionization of the sample 12 at various distances along the liquid jet 50 may be shown to correspond to different reaction times, i.e., $L_{jet}$ may include $L_1$ and $L_2$, where $L_2$ is greater than $L_1$ and corresponds to a later reaction time. While only two $L_{jet}$ measurements are specifically shown and may be sufficient for a first order reaction having a linear relation, one of ordinary skill in the art would readily appreciate that additional $L_{jet}$ distances may be evaluated and, indeed, necessary to properly analyze higher order reactions or to obtain a statistical number of data points.

Once the particular $L_{jet}$ is established, the nebulizing ionizer 10 is activated, thereby creating the spray 28 that desorbs and ionizes at least a portion of the sample 12 within the liquid jet 50 toward the mass analyzer 30. The desorbed and ionized sample may then be analyzed and the spectrum generated at each $L_{jet}$.

While in some embodiments the various measurement of $L_{jet}$ may include movement of the nebulizing ionizer 10 and/or the mass analyzer 30 relative to the liquid jet 50, it would be readily appreciated that because of the sensitivity of these components to environmental conditions and movement, it may be advantageous to instead move the Tee-mixer 64 relative to the nebulizing ionizer 10 and the mass analyzer 30. In one embodiment, though not shown, a vertical micrometer may be used to adjust the length of $L_{jet}$. In yet other embodiments, varying the injection rate provided by the syringe pumps 66, 68 may be adjusted to vary the rate at which the at least two reactants 52, 54 enter the mixer 64 and thus the speed of the continuous liquid jet 50. The speed of the continuous liquid jet 50 may then be correlated to different reaction times for reaction kinetic analysis. Accordingly, a controller 78 (FIG. 1A) that is programmed to vary the rate at which the at least two reactants 52, 54 enter the mixer 64 may be used.

Figure 2:
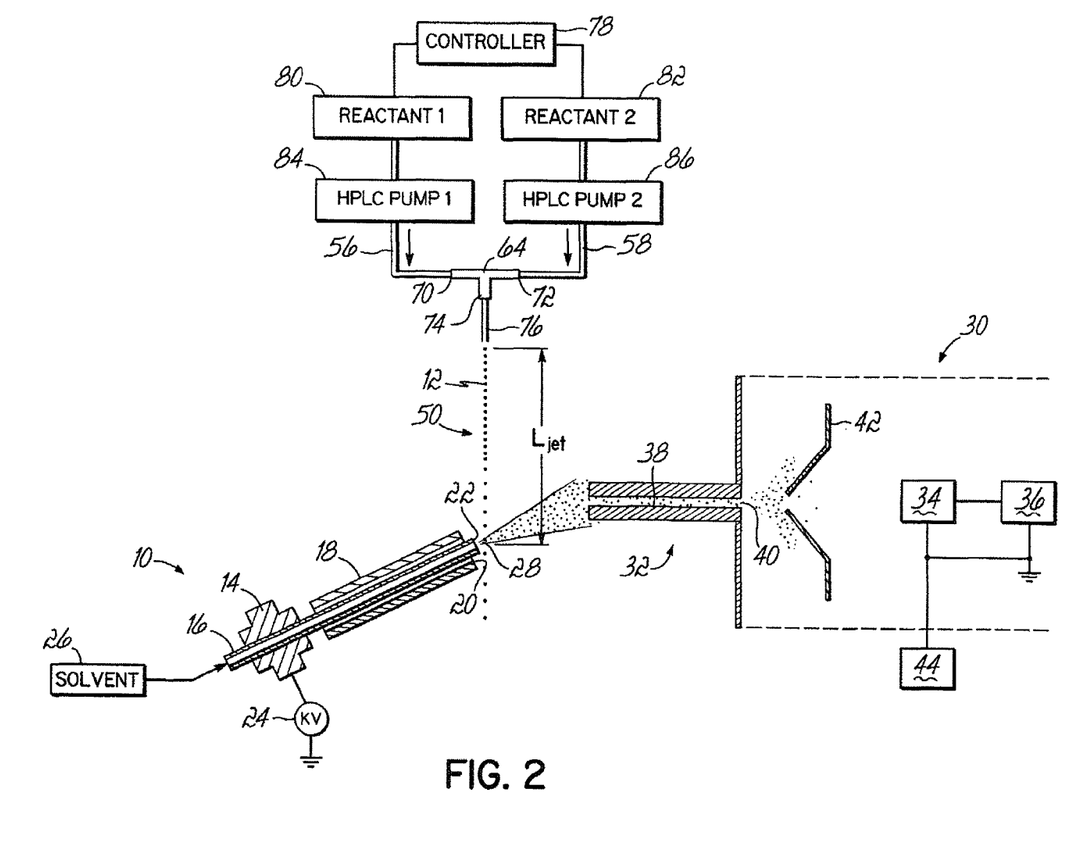
FIG. 2 is a schematic representation of another exemplary embodiment of an apparatus for time-resolved liquid jet desorption electrospray ionization mass spectroscopy study.

With reference now to FIG. 3, a time-resolved mass spectrometry device in accordance with another embodiment of the invention is described, where like reference numbers refer to like elements. As shown, first and second reactants 80, 82 from separate reactant sources are actively pumped into the capillaries 56, 58. More specifically, first and second High Performance Liquid Chromography ("HPLC") pumps 84, 86 are used to pump the reactants 80, 82 from a suitable reservoir or storage container and into the capillaries 56, 58. The HPLC pumps 84, 86 may be operated at a rate that ranges from about 0.1 mL/min to about 3 mL/min, for example, 2.0 mL/min. In this case, the dead time for mixing was reduced to 2.45 ms due to the increased flow rate. Various suitable pumps may be used (not just HPLC pumps but also syringe pumps and so forth), one particular pump includes the commercially-available HPLC pump from a Perkin Elmer HPLC system (Perkin Elmer, Shelton, Conn.) that is operated without a chromotography column.

The reactants 80, 82 combine within the Tee-mixer 64 and are ejected as the continuous liquid jet 50 of the sample 12. In this particular embodiment, the nebulizing ionizer 10 is angled upwardly with respect to the continuous liquid jet 50 whereas the embodiment illustrated in FIG. 1A was angled downwardly. Thus, it will be appreciated that the nebulizing ionizer 10 may be angled, as appropriate, in order to maximize the signal achieved from the mass analyzer 30.

It is well known in the art how to determine which spectral peaks within the spectrum correspond to a particular ion of interest. Accordingly, the relative abundancies of the ions of interest are compared and related, such as by the pseudo first order reaction equation, to calculate the reaction rate. The invention will be further appreciated in light of the following examples.

Example 1

The rate of acid-induced unfolding of cytochrome c was investigated using a device similar to the exemplary embodiment of FIG. 1A. A rate of conformational change for cytochrome c may be generally expressed as:

$$F \leftrightarrow U$$

where F designates the folded protein conformation and U designates the unfolded protein conformation.

In that regard, a sample of cytochrome c in $H_2O$ was loaded into the first syringe 52 and a 4% acetic acid solution was loaded into the second syringe 54. Fast mixing occurred within the Tee-mixer 64. The liquid jet 50 was sampled for DESI-MS analysis at $L_{jet}$ distances of about 0.5 cm, 1.0 cm, 1.5 cm, 2.0 cm, 2.5 cm, and 3.0 cm, which are calculated to correspond to reaction times of 10.5 ms, 12.0 ms, 13.5 ms, 15.0 ms, 16.5 ms, and 18.0 ms, respectively.

Figure 3A:
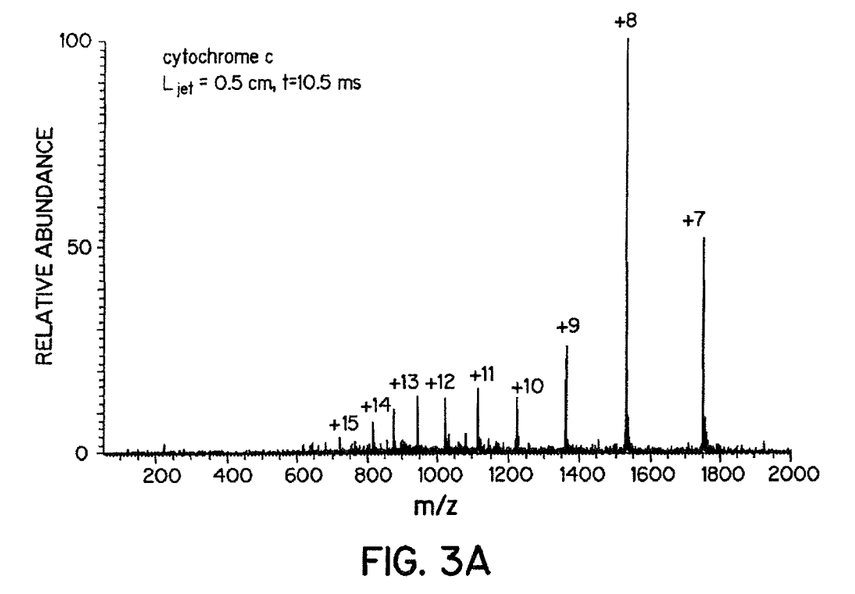
FIGS. 3A and 3B are exemplary spectra of an acid-induced unfolding of cytochrome c at two reaction time points, corresponding to the sampling distance of $L_1$ and $L_2$, respectively.

FIG. 3A illustrates an exemplary spectrum acquired at =0.5 cm (10.5 ms) and demonstrates dominating peaks having m/z values ranging between +7 and +10, corresponding to the native protein ions, i.e., folded cytochrome c. Lower intensity peaks having m/z values ranging from +11 to +16 indicate a relatively smaller fraction of unfolded protein ions.

Figure 3B:
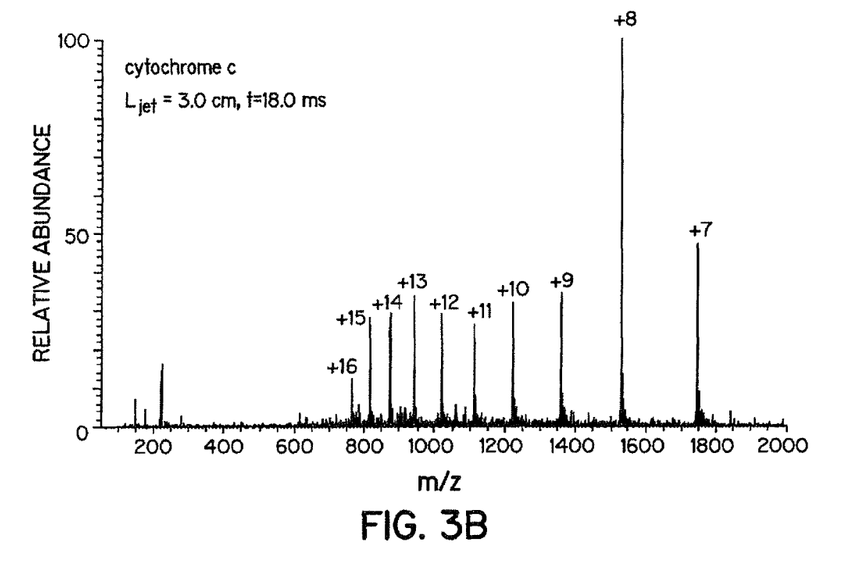

FIG. 3B illustrates an exemplary spectrum acquired at $L_{jet}$=3.0 cm (18.0 ms) and demonstrates significant increases in the relative abundances of those peaks having m/z values from +11 to +16, corresponding to the unfolded conformation of the cytochrome c.

Figure 3C:
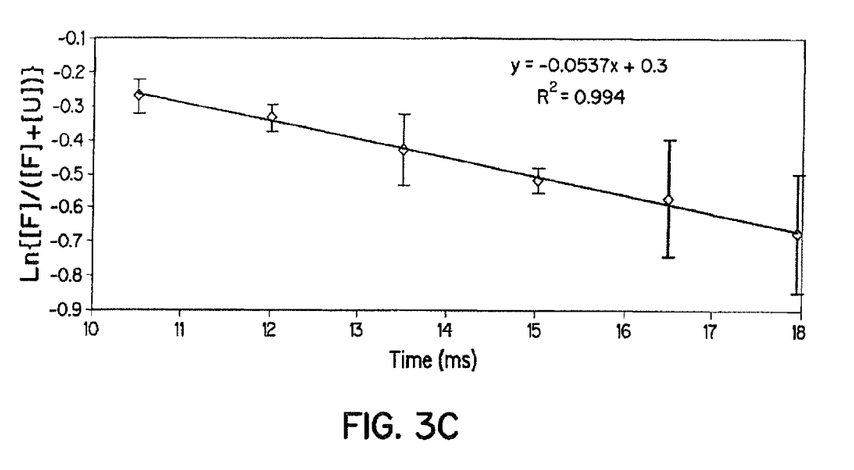
FIG. 3C is an exemplary measurement of a pseudo first order rate constant of the acid-induced unfolding of cytochrome c.
Figure 4A:
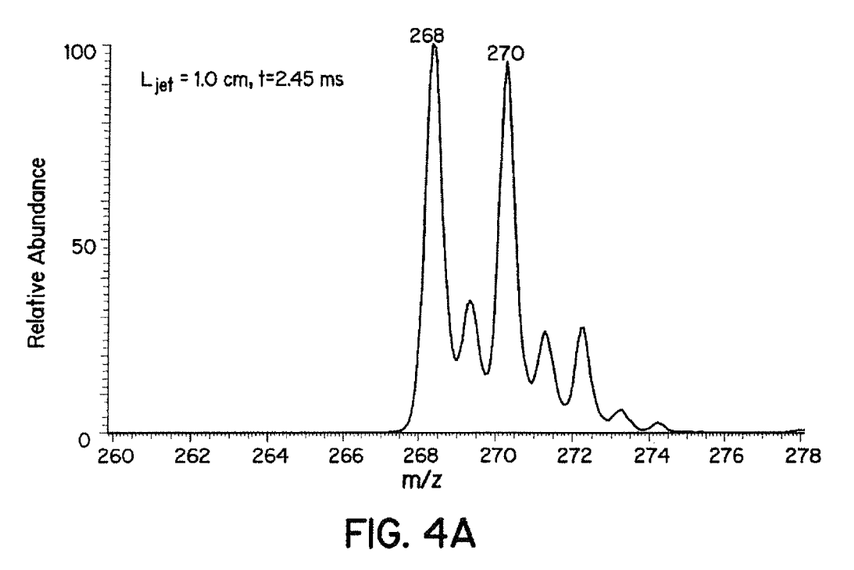
FIGS. 4A-4D are exemplary spectra of the reduction of 2,6-dichlorophenolindophenol ("DCIP") by L-ascorbic acid (L-AA).
Figure 4B:
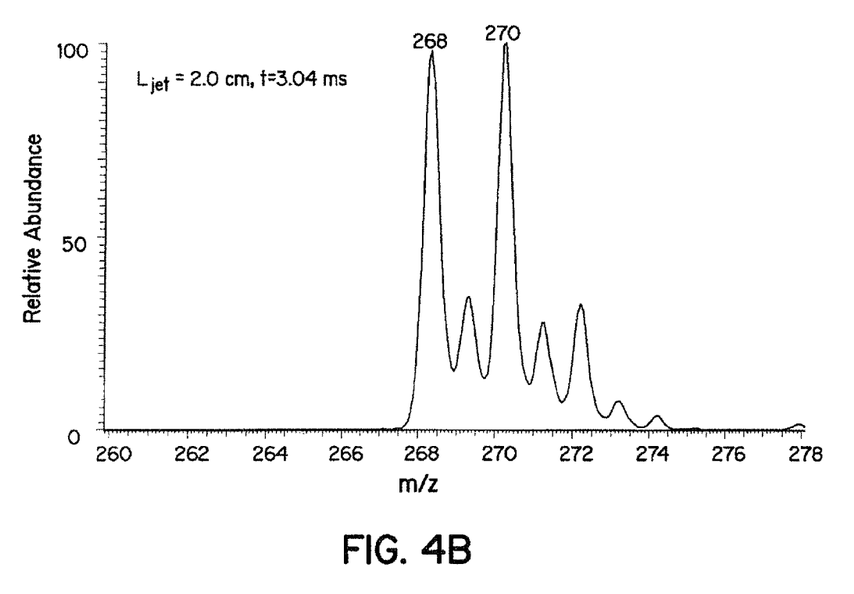
Figure 4C:
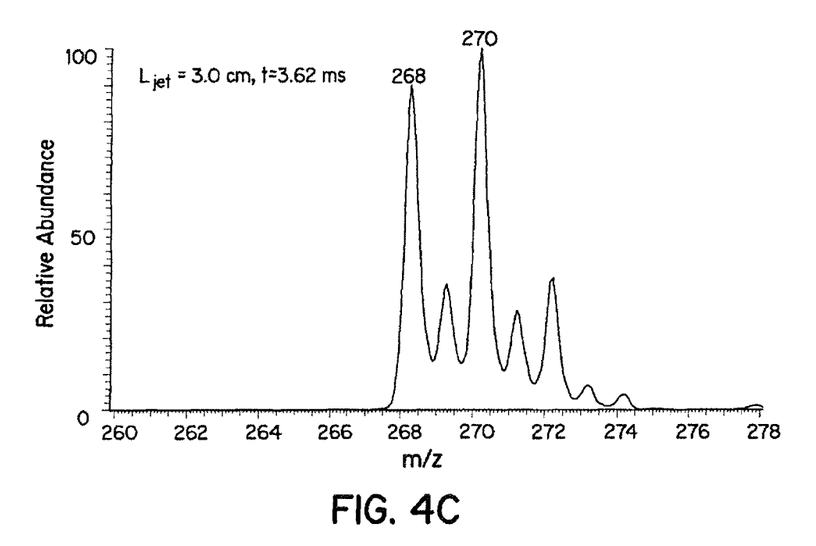
Figure 4D:
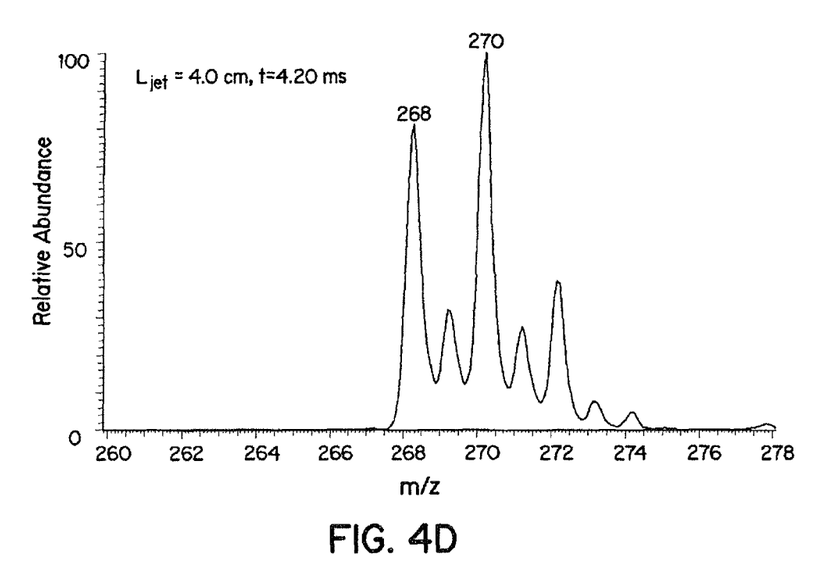

FIG. 3C shows the linear relationship:

$$\ln\left\{\frac{[F]}{[F]+[U]}\right\}$$

for modeling a pseudo first order reaction of acid-induced unfolding of cytochrome c. To determine the concentrations of the folded [F] and unfolded [U] conformations, the relative abundancies of ions having m/z values ranging between +7 and +10 or +11 and +16, respectively, were summed. Error bars in FIG. 2C were calculated by repeated measurements for each $L_{jet}$, as is well known by those of ordinary skill in the art. From FIG. 2C, the rate constant for the acetic acid induced unfolding of cytochrome c was found to be 53.7 $s^{-1}$.

Example 2

The rate of L-ascorbic acid ("L-AA") induced reduction of 2,6-dichlorophenolindophenol ("DCIP") was investigated using a device that is similar to the exemplary embodiment of FIG. 2. The reaction under investigation may be expressed as follows:

A solution of 40 mM LAA in 20 mM HCl and a solution of 0.2 mM DCIP in $H_2O$ were pumped via the HPLC pumps 84, 86 at a flow rate of 1.0 mL/min into the Tee-mixer 64 to produce a continuous jet 50 having a pH of 2.0. Desorption and ionization occurred with the DESI sprayer 10 having a spray solvent 26 of 20 mM aqueous $NH_4OAc$ buffer having a pH of 7.0 under nitrogen gas. An LCQ DECA mass spectrometer 30 (Thermo Finnigan, San Jose, Calif., USA) was used for mass analysis.

A vertical micrometer adjusted the height of Tee-mixer 64 relative to the DESI sprayer 10 and the mass spectrometer 30 for DESI-MS analysis. $L_{jet}$ distances of 1.0 cm, 1.5 cm, 2.0 cm, 2.5 cm, 3.0 cm, 3.5 cm, and 4.0 cm were calculated to correspond to reaction times 2.45 ms, 2.75 ms, 3.04 ms, 3.33 ms, 3.62 ms, 3.91 ms, and 4.20 ms, respectively. At longer $L_{jet}$, the concentration of oxidized DCIP decreased, as indicated by a drop in intensity of the corresponding protonated oxidized DCIP (m/z 268). Because DCIP includes two chlorine atoms, the oxidized DCIP includes two additional isotopic peaks at m/z 270 and m/z 272, with a relative intensity ratio of the three peaks being 9:6:1. Reduced DCIP is observed at m/z 270, which overlaps with one isotopic peak of the oxidized species.

Calculation of the rate constant included a determination from the relative abundance ratio, R, of the m/z 268 and m/z 270 peaks of the remaining concentration of oxidized DCIP at each $L_{jet}$ as follows:

$$R = \frac{\frac{9}{16}Ci}{\frac{6}{16}Ci + \frac{9}{16}(C_0 - C)}$$

where C is the remaining concentration of oxidized DCIP at a particular $L_{jet}$, $C_0$ is the initial concentration of oxidized DCIP (here is 0.1 mM), i is the relative ionization efficiency (here is 1.09), and $C_0$–C is the concentration of reduced DCIP product.

Representative spectra are shown in FIGS. 4A-4D and correspond to $L_{jet}$ values of 1.0 cm, 2.0 cm, 3.0 cm, and 4.0 cm, respectively.

Figure 5:
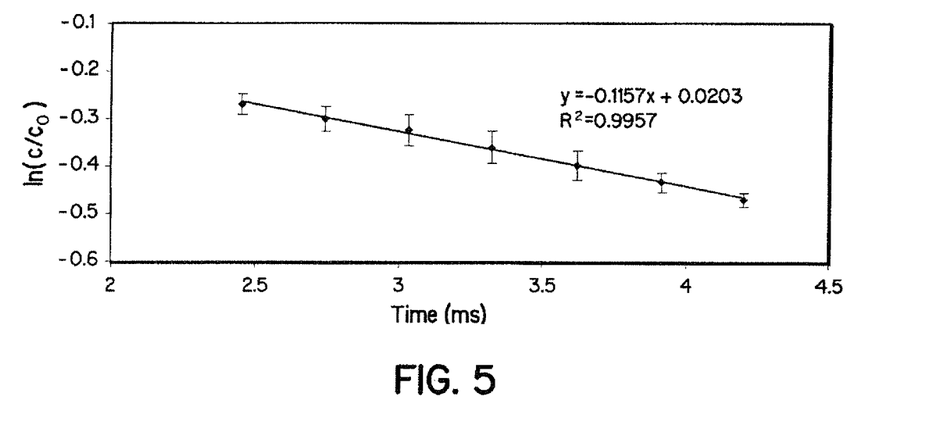
FIG. 5 is an exemplary measurement of a pseudo first order rate constant of the reduction of DCIP.

A pseudo first order rate constant, k, was derived by plotting $\ln(C/C_0)$ versus time (ms), is illustrated in FIG. 5, and was determined to be 116 $s^{-1}$. This value is in good agreement with a pseudo-first order reaction rate constant of 105 $s^{-1}$, which was determined using a conventional, commercially-available stopped-flow UV-Vis Spectrometer (Applied Photophysics, Model SZ.18MV) using the same experimental conditions as the above noted DESI-MS experiment. More specifically, the 4.0 mM L-AA in 20 mM HCl and 0.2 mM DCIP in $H_2O$ were pneumatically driven from two 5.0 mL Hamilton syringes into a mixing cell.

The various embodiments of the invention are directed to time-resolved mass spectroscopy techniques that are configured to provide micro-second time resolution for kinetic chemical studies. The embodiments enable the study of fast chemical reactions with high specificity and without the need for chromophoric substrates or other detection intermediates.

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A method of measuring a rate constant of a chemical reaction using mass spectrometry in microsecond time resolution, the method comprising:
   supplying at least two reactants to a mixer to form a mixture;
   wherein said reactants in said mixture react upon mixing;
   ejecting a continuous liquid jet comprised of said mixture from the mixer;
   subjecting said continuous liquid jet to a first liquid sample by positioning an ionizer at a first distance from said mixer along the continuous liquid jet and desorbing at least a portion of the continuous liquid jet as a first ionized sample;
   directing the first ionized liquid sample to a mass analyzer and obtaining a first spectrum of said first ionized liquid sample, said spectrum showing a first concentration f at least one ion of interest;
   subjecting said continuous liquid jet to a second liquid sample desorption ionization mass spectrometry by positioning the ionizer at a second distance from said mixer along the continuous liquid jet and desorbing at least a portion of the continuous liquid jet as a second ionized sample, wherein the second distance from said mixer is different than the first distance from said mixer;
   directing the second ionized liquid sample to the mass analyzer and obtaining a second spectrum of said second ionized liquid sample, said second spectrum showing a second concentration of at least one ion of interest; and
   comparing said first spectrum with said second spectrum to determine said rate constant.

2. The method of claim 1, wherein positioning the nebulizing ionizer includes moving the mixer relative to the nebulizing ionizer.

3. The method of claim 1, wherein supplying the at least two reactants further comprises:
   directing a first reactant from a first syringe to a first inlet of the mixer; and
   directing a second reactant from a second syringe to a second inlet of the mixer.

4. The method of claim 1, wherein directing the first and second reactants is driven by separate syringe pumps or separate HPLC pumps.

5. The method of claim 1, wherein the mixer is a Tee-mixer.

6. A method of measuring the rate constant of a chemical reaction using mass spectrometry in microsecond time resolution, the method comprising:
   supplying at least two reactants to a mixer at a first flow rate to form a mixture wherein said reactants in said mixture react upon mixing;
   ejecting a continuous liquid jet comprised of said mixture from the mixer at a first speed;
   subjecting said continuous liquid jet to a first liquid sample desorption ionization mass spectrometry by positioning an ionizer along the first continuous liquid jet so as to desorb at least a portion of the first continuous liquid jet as a first ionized sample and into a mass analyzer; and obtaining a first spectrum of said first ionized sample, said spectrum showing a first concentration f at least one ion of interest;
   adjusting the supplying of at least one of the at least two reactants to a second flow rate such that said continuous liquid jet is ejected from the mixer at a second speed;
   subjecting said second continuous liquid jet to a second liquid sample desorption ionization mass spectrometry by desorbing at least a portion of a second ionized liquid sample with the nebulizing ionizer and into the mass analyzer and obtaining a second spectrum of said second ionized liquid sample, said spectrum showing a second concentration of said at least one ion of interest and comparing said first spectrum said with said spectrum to determine said rate constant.

7. The method of claim 6, wherein the at least two reactants are supplied by first and second syringes, respectively, to first and second HPLC systems, respectively.

8. The method of claim 6 further comprising:
   controlling the supplying of the at least two reactants with a controller to provide the first flow and second flow rates.

9. The method claimed in claim 1 further comprising determining a first reaction time comprising a first time from which said mixture is mixed in said mixer until said first ionized liquid sample is directed to said mass analyzer;
   and determining a second reaction time comprising a second time from which said mixture is mixed in said mixer until said second ionized liquid sample is directed to said mass analyzer.

10. The method claimed in claim 6 comprising determining a first reaction time comprising a first time from which said mixture is mixed in said mixer until said first ionized liquid sample is directed to said mass analyzer;
   and determining a second reaction time comprising a second time from which said mixture is mixed in said mixer until said second ionized liquid sample is directed to said mass analyzer.

* * * * *